(12) United States Patent
Babkin et al.

(10) Patent No.: US 9,408,655 B2
(45) Date of Patent: Aug. 9, 2016

(54) CRYOABLATION APPARATUS WITH ENHANCED HEAT EXCHANGE AREA AND RELATED METHOD

(75) Inventors: Alexei Babkin, Albuquerque, NM (US); Peter Littrup, Bloomfield Hills, MI (US); William Nydam, Rancho Santa Fe, CA (US)

(73) Assignee: CryoMedix, LLC, San Diego, CA (US)

( * ) Notice: Subject to any disclaimer, the term of this patent is extended or adjusted under 35 U.S.C. 154(b) by 597 days.

(21) Appl. No.: 13/980,632

(22) PCT Filed: Oct. 27, 2011

(86) PCT No.: PCT/US2011/058094
§ 371 (c)(1),
(2), (4) Date: Jul. 19, 2013

(87) PCT Pub. No.: WO2012/058430
PCT Pub. Date: May 3, 2012

(65) Prior Publication Data
US 2013/0331829 A1    Dec. 12, 2013

Related U.S. Application Data

(60) Provisional application No. 61/407,168, filed on Oct. 27, 2010.

(51) Int. Cl.
*A61B 18/02*    (2006.01)
(52) U.S. Cl.
CPC .......... *A61B 18/02* (2013.01); *A61B 2018/0268* (2013.01)
(58) Field of Classification Search
CPC .................. A61B 18/02; A61B 2018/0268

USPC ....................................................... 606/20–50
See application file for complete search history.

(56) References Cited

U.S. PATENT DOCUMENTS

| | | | |
|---|---|---|---|
| 4,249,923 A | 2/1981 | Walda | |
| 4,946,460 A | 8/1990 | Merry et al. | |
| 5,207,674 A | 5/1993 | Hamilton | |
| 5,305,825 A | 4/1994 | Roehrich et al. | |
| 5,334,181 A * | 8/1994 | Rubinsky | A61B 18/02 606/20 |
| 5,520,682 A | 5/1996 | Baust et al. | |

(Continued)

OTHER PUBLICATIONS

Maybody, et al., Image-Guided Percutaneous Cryoablation of Renal Tumors, Tech Vasc Interventional Rad (2007), vol. 10, pp. 140-148.

(Continued)

*Primary Examiner* — Michael Peffley
*Assistant Examiner* — Khadijeh Vahdat
(74) *Attorney, Agent, or Firm* — Convergent Law Group LLP; Rick Batt

(57) ABSTRACT

A cryoablation apparatus includes a distal energy delivery section to facilitate energy transfer to the tissue, resulting in faster achievement of tissue target temperatures. The energy delivery section includes a first heat exchange region and a second heat exchange region having a different heat exchange efficiency than the first heat exchange region. The first heat exchange region may comprise an increased surface area along a radial portion or length of the cryoprobe in contact with surrounding tissue. The heat exchange region may include ridges, texture, threads, and microtubes which serve to increase the thermal-contacting surface area and provide enhanced cryoenergy to the tissue.

17 Claims, 14 Drawing Sheets

(56) References Cited

U.S. PATENT DOCUMENTS

| | | |
|---|---|---|
| 5,573,532 A | 11/1996 | Chang et al. |
| 5,674,218 A | 10/1997 | Rubinsky et al. |
| 5,733,247 A | 3/1998 | Fallon |
| 5,787,715 A | 8/1998 | Dobak, III et al. |
| 5,899,898 A | 5/1999 | Arless et al. |
| 5,946,920 A | 9/1999 | Clarke |
| 5,956,958 A | 9/1999 | Dobak, III et al. |
| 5,978,697 A | 11/1999 | Maytal et al. |
| 6,074,572 A | 6/2000 | Li et al. |
| 6,237,355 B1 | 5/2001 | Li |
| 6,241,722 B1 | 6/2001 | Dobak |
| 6,270,493 B1 | 8/2001 | Lalonde |
| 6,283,959 B1 | 9/2001 | Lalonde et al. |
| 6,355,029 B1 | 3/2002 | Joye et al. |
| 6,471,694 B1 | 10/2002 | Kudaravalli et al. |
| 6,485,422 B1 | 11/2002 | Mikus et al. |
| 6,530,234 B1 | 3/2003 | Dobak, III et al. |
| 6,530,946 B1 | 3/2003 | Noda et al. |
| 6,537,271 B1 | 3/2003 | Murray et al. |
| 6,551,309 B1 | 4/2003 | LePivert |
| 6,679,081 B2 | 1/2004 | Marsala |
| 6,685,720 B1 | 2/2004 | Wu et al. |
| 6,726,653 B2 | 4/2004 | Noda et al. |
| 6,773,408 B1 | 8/2004 | Acker et al. |
| 6,893,433 B2 | 5/2005 | Lentz |
| 6,893,653 B2 | 5/2005 | Abraham et al. |
| 6,904,305 B2 | 6/2005 | Tsekos |
| 6,972,015 B2 | 12/2005 | Joye et al. |
| 6,981,382 B2 | 1/2006 | Lentz et al. |
| 6,984,233 B2 | 1/2006 | Hooven |
| 7,004,936 B2 | 2/2006 | Ryba et al. |
| 7,022,120 B2 | 4/2006 | LaFontaine |
| 4,602,623 A1 | 7/2006 | Allen, Jr. |
| 7,081,111 B2 | 7/2006 | Svaasand et al. |
| 7,192,426 B2 | 3/2007 | Baust et al. |
| 7,220,252 B2 | 5/2007 | Shah |
| 7,648,497 B2 | 1/2010 | Lane |
| 2002/0010460 A1* | 1/2002 | Joye ................. A61B 18/02 606/21 |
| 2002/0032438 A1 | 3/2002 | Lafontaine |
| 2002/0083717 A1 | 7/2002 | Mullens et al. |
| 2002/0115989 A1 | 8/2002 | Abboud et al. |
| 2003/0024250 A1 | 2/2003 | Haas et al. |
| 2003/0055415 A1 | 3/2003 | Yu et al. |
| 2003/0181896 A1* | 9/2003 | Zvuloni ................. A61B 18/02 606/20 |
| 2003/0220634 A1 | 11/2003 | Ryba et al. |
| 2004/0215294 A1 | 10/2004 | Littrup et al. |
| 2005/0027334 A1 | 2/2005 | Lentz et al. |
| 2005/0038422 A1 | 2/2005 | Maurice |
| 2005/0182394 A1 | 8/2005 | Spero et al. |
| 2005/0203505 A1 | 9/2005 | Megerman et al. |
| 2005/0261753 A1 | 11/2005 | Littrup et al. |
| 2006/0004349 A1 | 1/2006 | Ryba et al. |
| 2006/0155268 A1 | 7/2006 | Amir et al. |
| 2006/0235375 A1 | 10/2006 | Littrup et al. |
| 2007/0031338 A1 | 2/2007 | Zabinski |
| 2007/0043342 A1 | 2/2007 | Kleinberger |
| 2007/0112251 A1 | 5/2007 | Nakhuda |
| 2007/0119190 A1 | 5/2007 | Yan |
| 2007/0277550 A1 | 12/2007 | Li et al. |
| 2008/0027420 A1 | 1/2008 | Wang et al. |
| 2008/0033419 A1 | 2/2008 | Nields et al. |
| 2008/0114344 A1 | 5/2008 | Xiao et al. |
| 2008/0119834 A1 | 5/2008 | Vancelette et al. |
| 2008/0119839 A1 | 5/2008 | Vancelette et al. |
| 2008/0119840 A1 | 5/2008 | Vancelette |
| 2008/0121759 A1 | 5/2008 | Behrens et al. |
| 2008/0125764 A1 | 5/2008 | Vancelette et al. |
| 2008/0161784 A1 | 7/2008 | Hogan et al. |
| 2009/0234345 A1 | 9/2009 | Hon |
| 2009/0270851 A1 | 10/2009 | Babkin |
| 2009/0287201 A1 | 11/2009 | Lalonde |
| 2010/0256621 A1* | 10/2010 | Babkin ................. A61B 18/02 606/21 |
| 2015/0018808 A1 | 1/2015 | Mihalik |
| 2015/0018809 A1 | 1/2015 | Mihalik |

OTHER PUBLICATIONS

PCT International Search Report and Written Opinion issued Mar. 27, 2012 for PCT/US2011/049287.

PCT International Search Report and Written Opinion issued May 4, 2010 for PCT/US2009/069046.

PCT International Examination Report issued Oct. 11, 2011 for PCT/US2010/029953.

PCT International Search Report and Written Opinion issued Jan. 26, 2011 for PCT/US2010/033070.

* cited by examiner

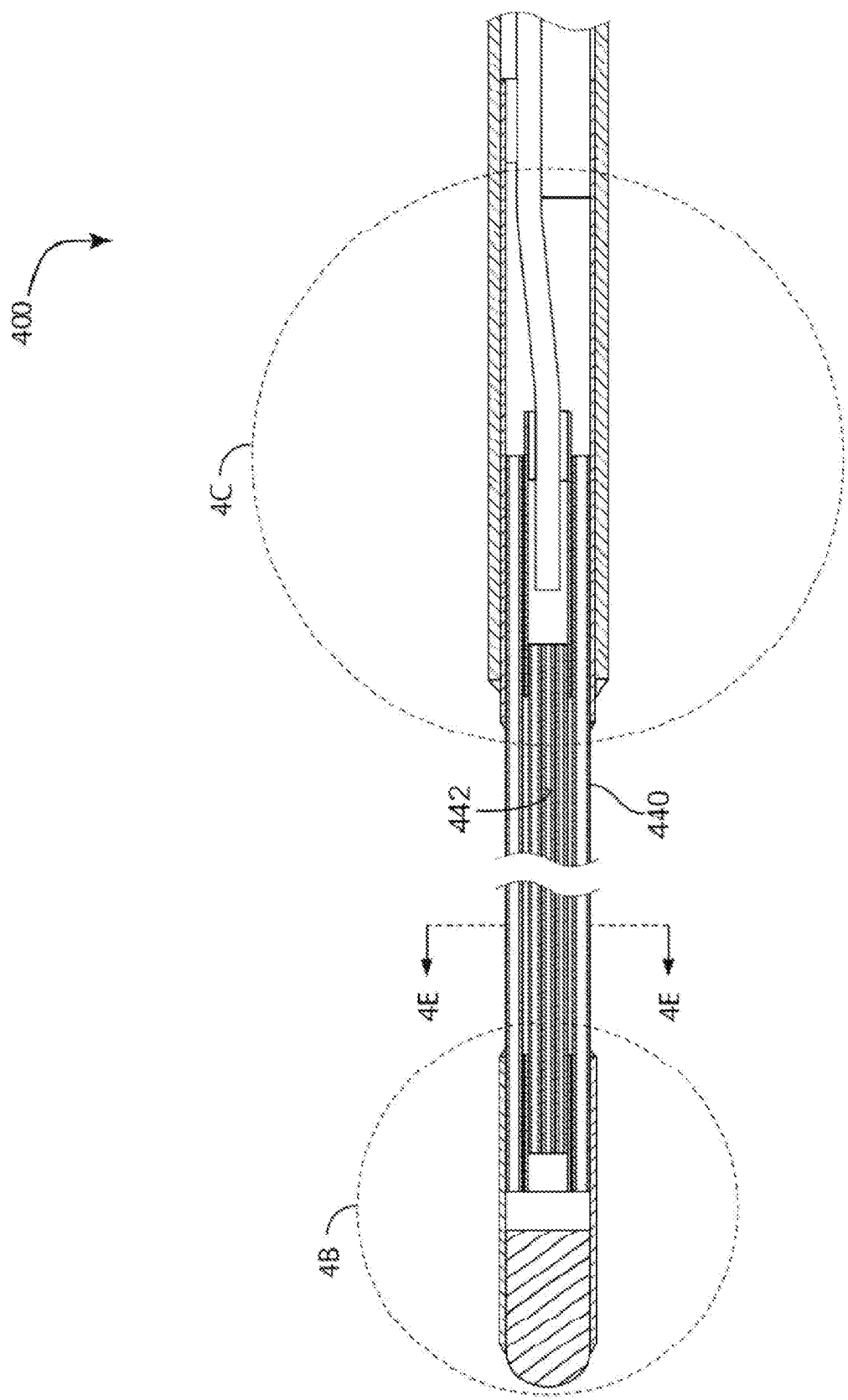

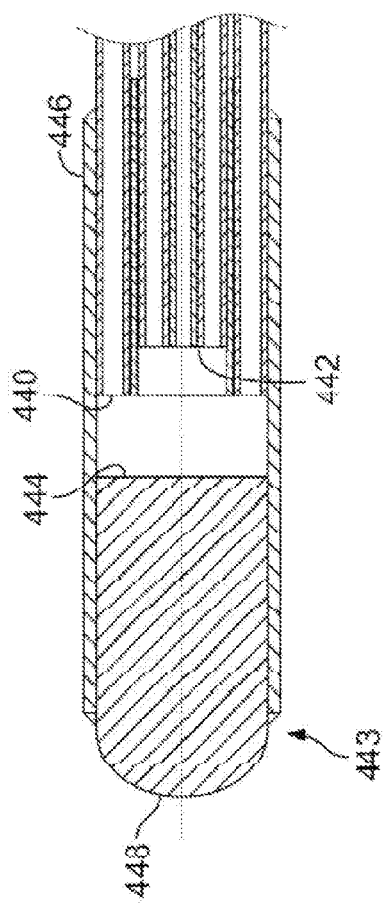
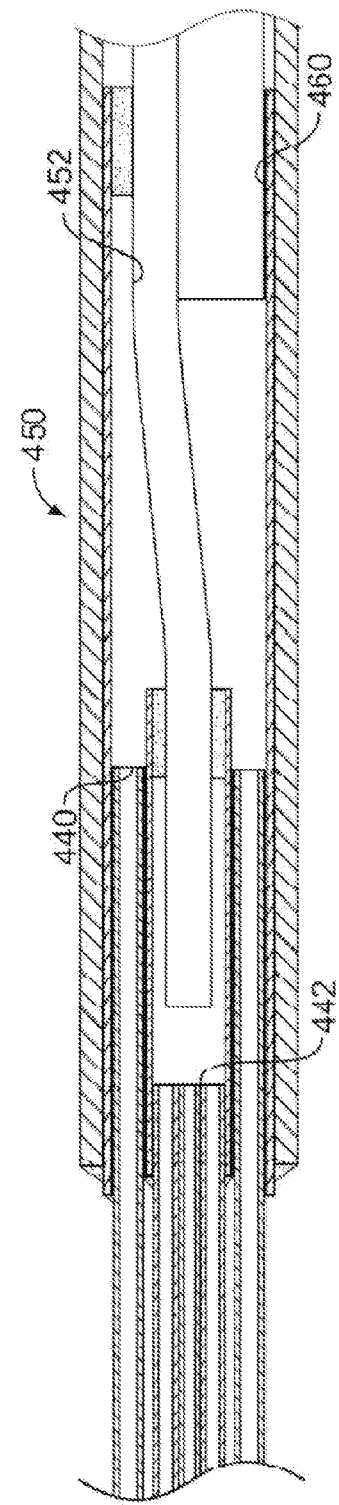

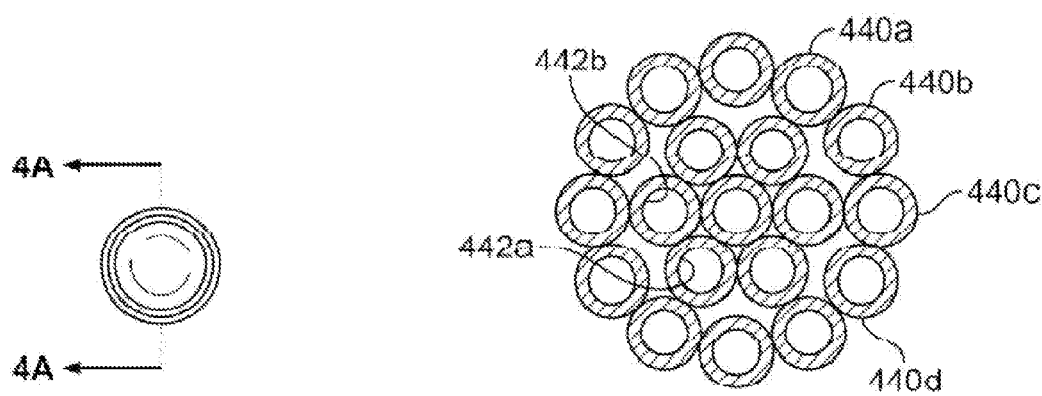
FIG. 4D
FIG. 4E
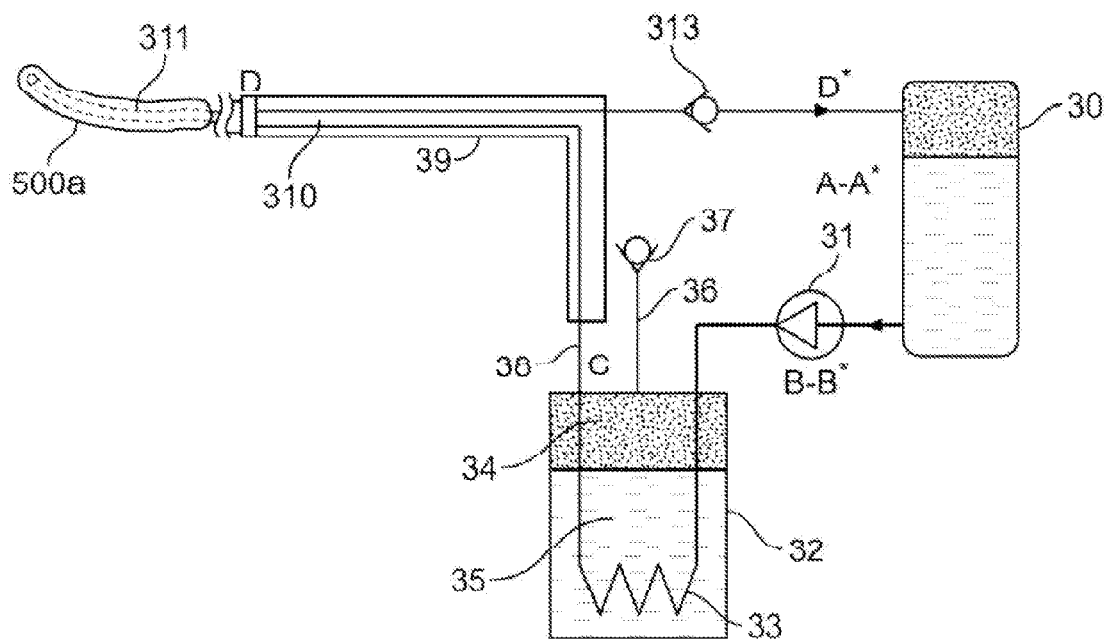
FIG. 5

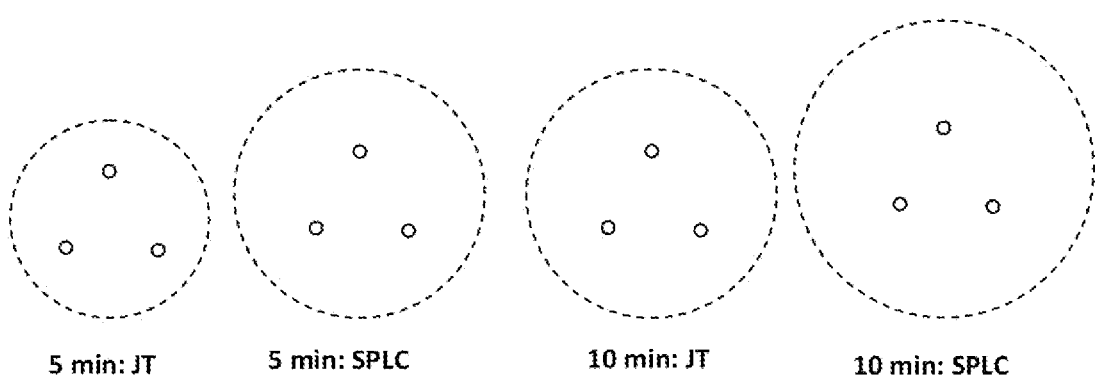

CRYOABLATION APPARATUS WITH ENHANCED HEAT EXCHANGE AREA AND RELATED METHOD

CROSS-REFERENCE TO RELATED APPLICATIONS

The present application claims the benefit of Provisional Application No. 61/407,168, filed Oct. 27, 2010, entitled "Cryogenic Instrument with Enhanced Heat Exchange Area for Improved Cryoablation Treatment".

STATEMENT OF GOVERNMENT SPONSORSHIP

This invention was made with government support under Grant No. 1R43CA141989-01-01 awarded by National Institute of Health. The government has certain rights in the invention.

BACKGROUND OF THE INVENTION

This invention relates to a cryoablation apparatus for treating biological tissues, and more particularly, to a cryoablation apparatus having an enhanced heat exchange distal end section.

Cryosurgical therapy involves application of extremely low temperature and complex cooling systems to suitably freeze the target biological tissues to be treated. Many of these systems use cryoprobes or catheters with a particular shape and size designed to contact a selected portion of the tissue without undesirably affecting any adjacent healthy tissue or organ. Extreme freezing is produced with some types of refrigerants that are introduced through the distal end of the cryoprobe. The distal surface of the cryoprobe is desirably in direct thermal contact with the target biological tissue to be treated.

In many situations, however, cryoablation of biological tissue requires a desired target temperature within the target tissue which is not in direct thermal contact with the cryoprobe. In such situations, the distance the target tissue is from the actual cryoprobe or cryocatheter is important. For example, deeper cancerous tumors seen by imaging (e.g., ultrasound, computed tomography, magnetic resonance) will generally be killed by two freeze cycles to a target temperature of −40° C. with an intervening passive thaw cycle. The faster that the −40° C. target temperature is achieved throughout the tumor, the greater the lethality or cytotoxicity of each freeze to the tumor. Assuming approximately one cryoprobe for each centimeter of tumor diameter, the usual freeze time is up to 10 min each, within interval passive thaw of 5 min., for a total of up to 25 min with current clinical cryotechnology. The visible ice margin of 0° C. thus generally needs to extend beyond 1 cm of tumor margins to achieve the target temperature −40° C. beyond all tumor margins. There is a great need for improving the speed of these procedures, the thermal conduction of target temperatures to deeper tissues further from the cryoprobe, as well as limiting the number of cryoprobes needed to cover a target tumor volume.

There are various known cryosurgical systems including, for example, liquid nitrogen and nitrous oxide type systems. Liquid nitrogen has a very desirable low temperature of approximately −200° C., but when it is introduced into the distal freezing zone of the cryoprobe which is in thermal contact with surrounding warm biological tissues, its temperature increases above the boiling temperature (−196° C.) and it evaporates and expands several hundred-fold in volume at atmospheric pressure and rapidly absorbs heat from the distal end of the cryoprobe. This enormous increase in volume results in a "vapor lock" effect when the internal space of the mini-needle of the cryoprobe gets "clogged" by the gaseous nitrogen. Additionally, in these systems the gaseous nitrogen is simply rejected directly to the atmosphere during use which produces a cloud of condensate upon exposure to the atmospheric moisture in the operating room and requires frequent refilling or replacement of the liquid nitrogen storage tank.

Nitrous oxide and argon systems typically achieve cooling by expansion of the pressurized gases through a Joule-Thomson expansion element such as a small orifice, throttle, or other type of flow constriction that are disposed at the end tip of the cryoprobe. For example, the typical nitrous oxide system pressurizes the gas to about 5 to 5.5 MPa to reach a temperature of no lower than about −85 to −65° C. at a pressure of about 0.1 MPa. For argon, the temperature of about −160° C. at the same pressure of 0.1 MPa is achieved with an initial pressure of about 21 MPa. The nitrous oxide cooling system is not able to achieve the temperature and cooling power provided by liquid nitrogen systems, but has some advantages because the inlet of high pressure gas at room temperature. When nitrous oxide or argon it reach the Joule-Thomson throttling component or other expansion device at the probe tip, cooling along the shaft and extension hoses are limited, which precludes the need for heavy thermal insulation of those system components. However, because of the insufficiently low operating temperature, combined with relatively high initial pressure, cryosurgical applications are strictly limited.

Additionally, the Joule-Thomson system typically uses a heat exchanger to cool the incoming high pressure gas using the outgoing expanded gas in order to achieve the necessary drop in temperature by expanding compressed gas. These heat exchanger systems are not compatible with the desired miniature size of probe tips that need to be less than 3 mm in diameter. Although an argon system is capable of achieving a desirable cryoablation temperature, argon systems do not provide sufficient cooling power and require very high gas pressures and volumes. These limitations are very undesirable for practical clinical applications.

Another cryoablation system uses a fluid at a near critical or supercritical state. Such cryoablation systems are described in U.S. Pat. Nos. 7,083,612 and 7,273,479. These systems have some advantages over previous systems. The benefits arise from the fluid having a gas-like viscosity. Having operating conditions near the critical point of nitrogen enables the system to avoid the undesirable vapor lock described above while still providing good heat capacity. Additionally, such cryosystems can use small channel probes.

However, challenges arise from use of a near-critical cryogen in a cryoablation system. In particular, there is still a significant density change in nitrogen once it is crossing its critical point (about 8 times)—resulting in the need for long pre-cooling times of the instrument. The heat capacity is high only close to the critical point and the system is very inefficient at higher temperatures requiring long pre-cooling times. Additionally, the system does not warm up (or thaw) the cryoprobe efficiently. Additionally, near-critical cryogen systems require a custom cryogenic pump which is more difficult to create and operate at cryogenic temperatures.

Still other types of cryosystems are described in the patent literature. U.S. Pat. Nos. 5,957,963; 6,161,543; 6,241,722; 6,767,346; 6,936,045 and International Patent Application No. PCT/US2008/084004, filed Nov. 19, 2008, describe malleable and flexible cryoprobes. Examples of patents describing cryosurgical systems for supplying liquid nitrogen, nitrous oxide, argon, krypton, and other cryogens or different combinations thereof combined with Joule-Thomson effect include U.S. Pat. Nos. 5,520,682; 5,787,715; 5,956,958; 6074572; 6,530,234; and 6,981,382.

Another type of cryoprobe is described in US Patent Publication 20080119840 to Vancelette. A cryoprobe tip has an increased surface area by having a corrugated, waved, or otherwise ridged configuration in its inner and outer surfaces. The cryoprobe, however, is shown having complex tubular cross-sections which may be difficult to manufacture. The complex cross-sections of the tube portion shown in Vancelette may complicate the return path of the refrigerant thus making heat exchange inside the probe less efficient.

Despite the above patent literature, an improved cryoablation apparatus having a small size and shape to achieve selective cooling of the target biological tissue is still desired. The more rapid cooling of target tissues to cytotoxic temperatures at distances of several millimeters from the point of tissue contact is crucial, but is not attained by cooling capacity or low probe surface temperatures. Cryogenic systems with high cooling capacities, such as liquid nitrogen, near critical or single phase liquid cooling systems require faster and more reliable cryoablation procedures.

An improved cryoablation apparatus having a tip that can be placed in direct contact with the target biological tissue to be thermally treated, and to form an ice ball on the target tissue for a controlled period of time, and that increases the effectiveness of the cryosurgical treatment is still desired.

An improved cryoablation apparatus having cryoablation tip which can operate with a single phase liquid refrigerant is still desired.

SUMMARY OF THE INVENTION

A cryoablation apparatus for treating tissue comprises an elongate shaft having a distal energy-delivery section and a distal tip; at least one active lumen extending through the distal energy-delivery section for transporting a refrigerant towards the distal tip; at least one return lumen extends through the distal energy-delivery section for transporting the refrigerant away from the distal tip. The distal energy-delivery section comprises a first heat exchange region and a second heat exchange region having a different heat transfer efficiency than the first heat exchange region such that the heat exchange efficiency varies lengthwise along the distal energy-delivery section of the elongate shaft.

In another embodiment the first heat exchange region may have a different surface area than the second heat exchange region. The first heat exchange region may be distal to the second heat exchange region and the first heat exchange region has a greater surface area than that of the second heat exchange region.

In another embodiment the first heat exchange region has a first length, and the first length ranges from 2 to 6 cm.

In another embodiment the first heat exchange region has a first length, and the second heat exchange region has a second length, and the first length is different than the second length. The outer surface of the first heat exchange region may have an exterior feature or means selected from the group consisting of ridges, grooves, and threads.

In another embodiment the exterior feature is a corrugation and has a characteristic height in the range of 2 to 5 mm. The elongate shaft may be rigid or flexible, and may have an inner surface which is substantially smooth and ridgeless. The interior surface may have the same or a different surface structure than the exterior surface.

In another embodiment a closed loop, single phase, liquid refrigerant cryoablation system for treating tissue comprises (a) a container holding the liquid refrigerant at an initial pressure and initial temperature; (b) a liquid pump operable to increase the pressure of the liquid refrigerant to a predetermined pressure thereby forming a compressed liquid refrigerant;(c) a cooling device operable to cool the compressed liquid refrigerant to a predetermined cryogenic temperature, the predetermined cryogenic temperature being lower than the initial temperature; and (d) a cryoprobe coupled to the cooling device and adapted to receive the compressed liquid refrigerant. The cryoprobe comprises an elongate shaft having a distal energy-delivery section and distal tip. The energy delivery section includes at least one cooling lumen and at least one return lumen wherein the liquid refrigerant flows towards and away from the distal tip through the cooling and return lumens respectively and wherein the at least one lumen is fluidly coupled to the container thereby completing the loop of the liquid refrigerant without the liquid refrigerant evaporating as the refrigerant is transported along the loop. The distal energy-delivery section comprises a first heat exchange region having a first exterior geometry which enhances the heat exchange between the tissue and the distal energy-delivery section. The first exterior geometry is selected from the group consisting of ridges, corrugations, and threads. The distal energy-delivery section may comprise a second heat exchange region having a geometry different than the first exterior geometry.

In another embodiment the at least one cooling lumen comprises a plurality of cooling microtubes extending in an axial direction and which increase the effective surface area in the distal energy delivery section. The microtubes may be in the form of a twisted bundle. In another embodiment the microtubes are spaced about the circumference of the distal energy delivery section. The predetermined cryogenic temperature may be less than or equal to −140° C. The initial pressure may be between 0.2 to 1.5 MPa and the predetermined pressure may be between 0.6 to 2.0 MPa.

In another embodiment a cryoablation method for applying cryoenergy to tissue comprises the steps of: driving a liquid refrigerant along a first flowpath commencing at an outlet of a refrigerant container, through a cryoprobe having an energy delivery distal section, and back to an inlet of the refrigerant container wherein the liquid refrigerant remains in a liquid-only state along the first flowpath. The distal section of the cryoprobe is positioned in the vicinity of the tissue. Cryoenergy is transferred to the tissue through a first heat exchange area extending along the distal section of the cryoprobe. Cryoenergy is transferred to the tissue through a second heat exchange area extending along the distal section of the cryoprobe. The step of transferring cryoenergy to the tissue through a first heat exchange area may comprise delivering energy through a first surface area, the first surface area being larger than a second surface area of the second heat exchange region. The first surface area may be at least 1.1 to 3.0 larger than the surface area of the second area. The first surface area may include ridges. Also, the step of positioning may be carried out through one device selected from the group consisting of an endoscope, a visualization device and a steering device.

In another embodiment a plurality of cryoprobes are inserted in the tissue. The first heat exchange region of the first cryoprobe and the first heat exchange region of the at least second cryoprobe may be turned such that the first heat exchange region of the first cryoprobe faces the first heat exchange region of the at least second cryoprobe.

In another embodiment a cryoablation method for applying energy to a tissue comprises positioning the distal section of the cryoprobe in the vicinity of the tissue; forming a first ice structure about a first region of the distal section and in contact with the tissue wherein the first ice structure is formed by applying cryoenergy through the first region of the distal section; and forming a second ice structure about a second region of the distal section and in contact with the tissue wherein the second ice structure is formed by applying cryoenergy through the second region of the distal section. The first ice structure may have a different dimension than the second ice structure.

In another embodiment the shape of the first ice structure is one shape selected from the group consisting of a cylinder, sphere, and ovoid.

The description, objects and advantages of the present invention will become apparent from the detailed description to follow, together with the accompanying drawings.

BRIEF DESCRIPTION OF THE DRAWINGS

FIG. 4a is a cross sectional view of a distal section of a cryoprobe in accordance with the present invention.

FIG. 4b is an enlarged view of the distal tip shown in FIG. 4a.

FIG. 4c is an enlarged view of the transitional section of the cryoprobe shown in FIG. 4a.

FIG. 4d is an end view of the cryoprobe shown in FIG. 4a.

FIG. 4e is a cross sectional view taken along line 4e-4e illustrating a plurality of microtubes for transporting the liquid refrigerant to and from the distal tip of the cryoprobe.

FIGS. 5-7 show a closed loop, single phase, liquid refrigerant cryoablation system including a cryoprobe operating to generate various shapes of ice along its distal section.

FIGS. 13A-D show predicted ice ball growth at 5 minutes and 10 minutes respectively for various cryoprobes.

DETAILED DESCRIPTION OF THE INVENTION

Figure 1:
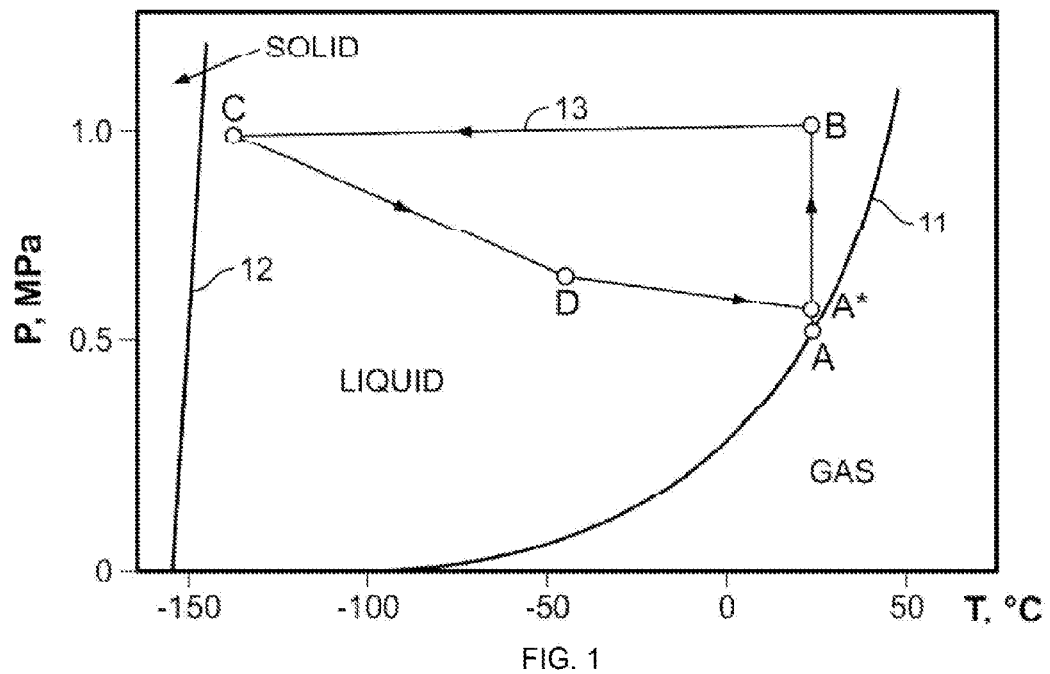
FIG. 1 is a phase diagram corresponding to a cooling cycle of a liquid refrigerant used in a cryoablation system.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

Cryotechnology described herein involves a number of parameters, features and/or steps to generate cytotoxic tissue temperatures throughout a target tissue volume. These include but are not limited to: 1.) the overall cooling capacity, or the ability to remove a measured wattage of heat generation; 2.) The lowest attainable temperature at the surface of the cryoprobe, or cryocatheter, in contact with the tissue, and; 3.) The surface area of the cryoprobe or cryocatheter in contact with the target tissue. Amongst other things, this latter characteristic is discussed herein in order to deliver an increased cooling capacity and low temperatures.

A cooling system for cryoablation treatment uses liquid refrigerants at low pressures and cryogenic temperatures to provide reliable cooling of the distal end of the cryoprobe and surrounding biological tissues to be ablated. Additionally, enhancing the heat exchange area at the distal section of the probe in combination with the use of liquid refrigerants as the cooling means can significantly increase cryoablation efficiency. This results in attaining target temperatures at a radial distance from the probe: 1.) faster, or 2.) further from the probe than with standard smooth surface probe technology.

Cooling systems preferably use a low pressure and cryogenic temperature refrigerant. An exemplary refrigerant is R218 refrigerant (octafluoropropane). To illustrate some of its properties, a phase diagram of R218 refrigerant is shown in FIG. 1. The axes of the diagram in FIG. 1 correspond to pressure p and temperature T of the R218 refrigerant, and include phase lines 11 and 12 that delineate the locus of points (p, T) where solid, liquid and gas states coexist. Although R218 is shown in connection with this embodiment, the invention may include use of other liquid refrigerants.

At point A of FIG. 1, the refrigerant is in a "liquid-vapor" equilibrium state in a storage tank or container. It has a temperature T0 of the environment, or slightly lower, at an initial pressure p0 of about 0.4 MPa. The closed loop cycle or refrigerant flowpath begins at the point where the liquid refrigerant exits the container or storage tank. In order for the refrigerant to remain in the liquid state throughout the entire cooling cycle and provide necessary pressure for the cryogen to flow through a cryoprobe or a catheter it is maintained at a slightly elevated pressure in the range from about 0.7 to 0.8 MPa (or in this example about 0.75 MPa). This corresponds to point B of FIG. 1. Point B is in the liquid area of R218 refrigerant. Further, the liquid is cooled by a cooling device (such as but not limited to a refrigerator) from point B to point C to a temperature Tmin that is shown by path 13 in FIG. 1. This temperature will be somewhat higher (warmer) than its freezing temperature at elevated pressure.

The cold liquid refrigerant at point C is used for cryoablation treatment and directed into the distal end of the cryoprobe that is in thermal contact with the biological tissue to be treated. This thermal contact leads to a temperature increase of the liquid refrigerant with a simultaneous pressure drop from point C to point D caused by the hydraulic resistance (impedance) of the microchannel distal end of the cryoprobe. The temperature of the return liquid is increased due to its environment. In particular, the temperature is increased due to thermal communication with the ambient surroundings and by slightly elevated pressure maintained by a device, e.g., a check valve (point A*). A small pressure drop of about 6 kPa is desirable to maintain the liquid phase conditions in a return line that returns the liquid refrigerant back to the storage tank. Finally, the cycle or flowpath is completed at the point where the liquid cryogen enters the storage tank. Re-entry of the liquid refrigerant may be through a port or entry hole in the container corresponding once again to point A of FIG. 1. The above described cooling cycle will be continuously repeated as desired.

Figure 2:
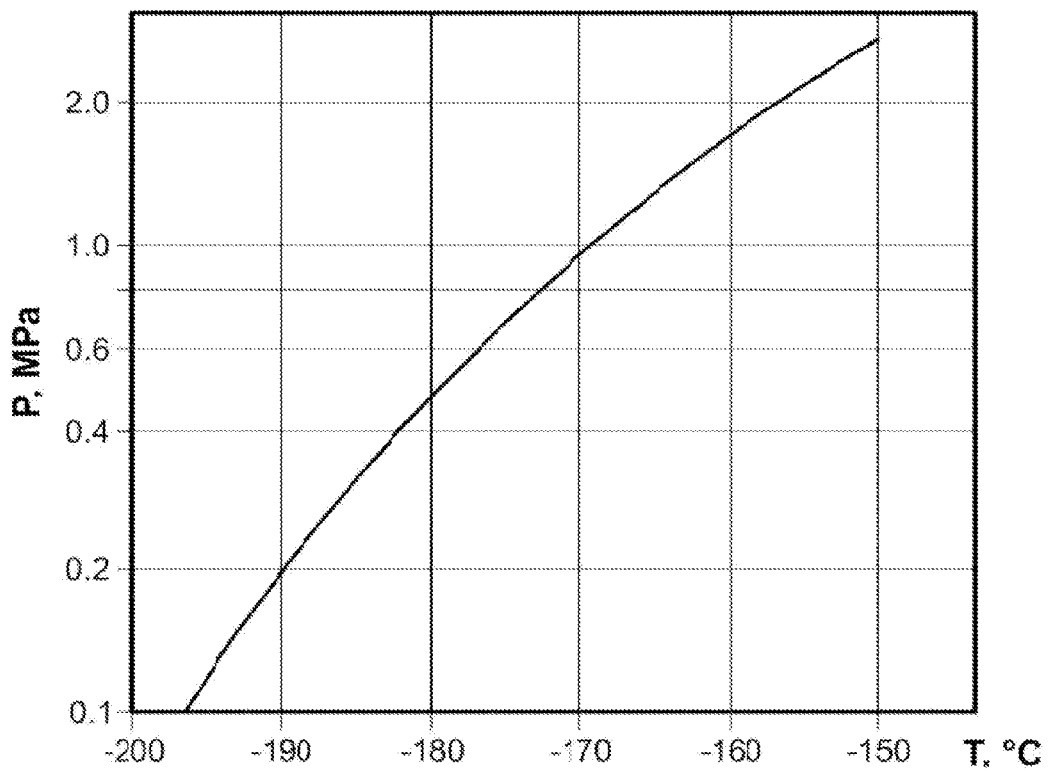
FIG. 2 is a diagram of the boiling temperature of liquid nitrogen as a function of pressure.

In some examples the cooling device or refrigerator can be a heat exchanger submerged in pressurized liquid nitrogen having a predetermined temperature Tmin depending on its pressure. The pressure may range from about 1.0 to 3.0 MPa. The liquid nitrogen can be replaced by liquid argon or krypton. In these cases, the predetermined temperatures Tmin will be obtained at pressures as low as about 0.1 to 0.7 MPa. An example of a "pressure, p—temperature, T" diagram of liquid nitrogen is shown in FIG. 2 defining the necessary predetermined temperature Tmin and corresponding pressure of the liquid refrigerant.

Figure 3:
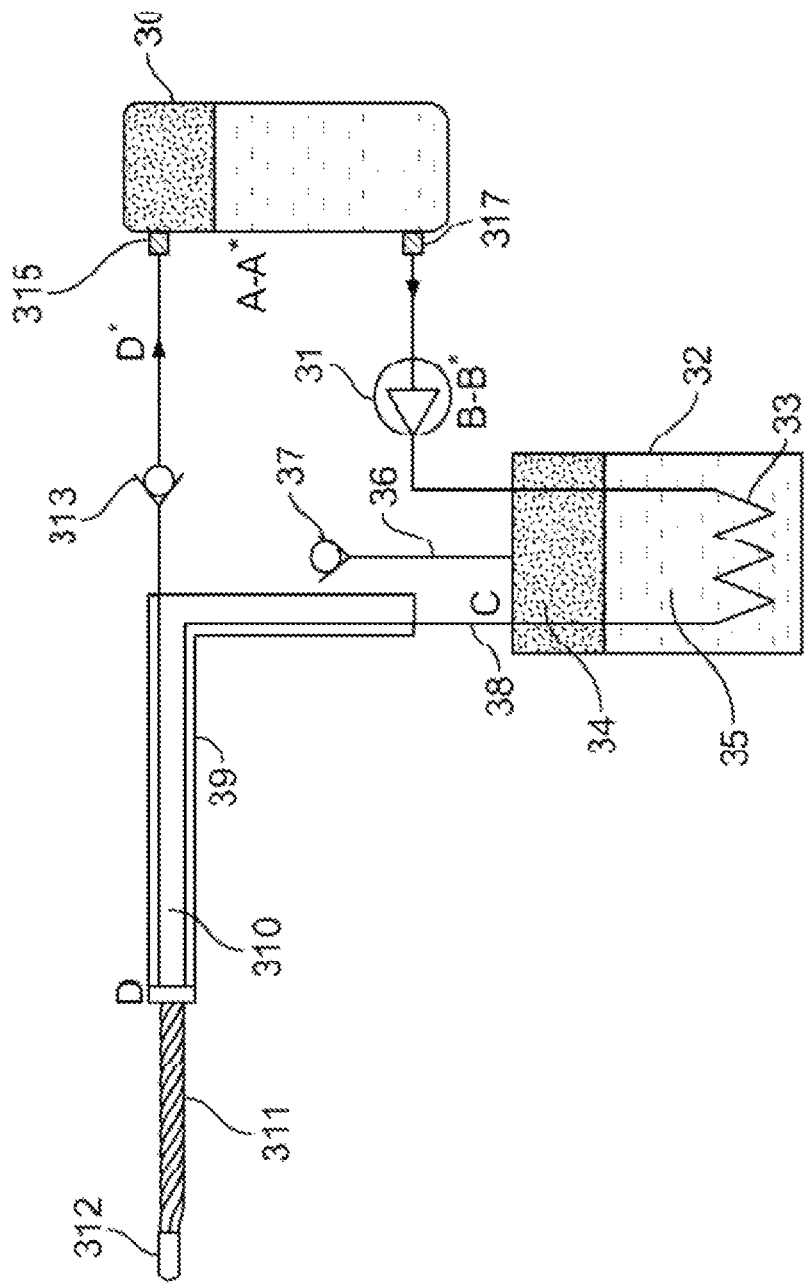
FIG. 3 is a schematic representation of a cooling system for cryoablation treatment comprising a plurality of microtubes in the cryoprobe.

An embodiment of the invention is to circulate a refrigerant in its operational liquid state, in a closed loop, without any evaporation, under low pressure and low temperature during the cooling cycle. This cooling system for cryoablation treatment is schematically shown in FIG. 3 where the liquid refrigerant at initial pressure p0 in container 30 is compressed by a liquid pump 31 under temperature T0 of the environment. Contrary to typical closed cooling cycles where cooling is achieved by evaporating refrigerants followed by high compression of the vapor, this pump can be very small in size as it drives the incompressible liquid. Further, the liquid refrigerant is transferred into the refrigerator 32 through the coiled portion 33 which is submerged in the boil-off cryogen 34, 35 provided by transfer line 36 and maintained under a predetermined pressure by check valve 37.

The boil-off cryogen has a predetermined temperature Tmin The coiled portion 33 of the refrigerator 32 is fluidly connected with multi-tubular inlet fluid transfer microtubes of the flexible distal end 311, so that the cold liquid refrigerant having the lowest operational temperature Tmin flows into the distal end 311 of the cryoprobe through cold input line 38 that is encapsulated by a vacuum shell 39 forming a vacuum space 310. The end cap 312 positioned at the ends of the fluid transfer microtubes provides fluid transfer from the inlet fluid transfer microtubes to the outlet fluid transfer microtubes containing the returned liquid refrigerant. The returned liquid refrigerant then passes through a check valve 313 intended to decrease the pressure of the returned refrigerant to slightly above the initial pressure p0. Finally, the refrigerant re-enters the container 30 through a port or opening 315 completing the flowpath of the liquid refrigerant. The system provides continuous flow of a refrigerant, and the path A-B-C-D-A*-A in FIG. 3 corresponds to phase physical positions indicated in FIG. 1. The refrigerant maintains its liquid state along the entire flowpath or cycle from the point it leaves the container through opening 317 to the point it returns to the storage tank or container via opening 315.

An example of a closed loop cryoprobe using a liquid refrigerant is described in patent application Ser. No. 12/425, 938, filed Apr. 17, 2009, and entitled "Method and System for Cryoablation Treatment".

Preferably, the minimum temperature (Tmin) is not lower than the freezing temperature of the liquid refrigerants to be used. For many practical applications in cryosurgery, the temperature of the distal end of the cryoprobe must be at least −1000 C or lower, and more preferably −1400 C or lower in order to perform a cryoablation procedure effectively. For diffuse variety of tissue ablations, this involves generating a cytotoxic temperature (e.g., −40° C.) as far and as fast as possible from the radial surface of the cryoprobe. There are several commonly used non-toxic refrigerants that are known to have normal freezing temperatures at about −1500 C or lower as shown in the following TABLE 1.

TABLE 1

| Refrigerant | Chemical formula | Molecular mass (kg/mol) | Normal freezing point (° C.) | Normal boiling point (° C.) |
| --- | --- | --- | --- | --- |
| R218 | $C_3F_8$ | 188.02 | −150 | −36.7 |
| R124 | $C_2HClF_4$ | 136.5 | −199 | −12.1 |
| R290 | $C_3H_8$ | 44.1 | −188 | −42 |

TABLE 1-continued

| Refrigerant | Chemical formula | Molecular mass (kg/mol) | Normal freezing point (° C.) | Normal boiling point (° C.) |
|---|---|---|---|---|
| R1270 | $C_3H_6$ | 42.08 | −185 | −47.7 |
| R600A | $i-C_4H_{10}$ | 58.12 | −159.5 | −11.8 |

As indicated above, enhancing the heat exchange area of the distal section of the cryoablation apparatus can improve ablation by extending the target temperature within the tissue further from the probe surface, or in less time, than current smooth surface technology. It is evident from the table above that SPLC has both a low cryogen temperature (i.e., <−150° C.) as well as high cooling capacity for even high thermal heat loads, or wattage situations. Various approaches to enhancing the heat exchange area are described herein.

Multi-Tubular Distal Section

For example, with reference to FIG. 4a, a distal section 400 of a cryoprobe includes an energy-delivery section made up of a plurality of tubes 440, 442. Transporting the liquid refrigerant through numerous microtubes can significantly increase the heat exchange rate to the surface area of the probe and thus to the biological tissue to be treated.

Cross sections of one example of a multitubular apparatus to increase heat exchange are shown in FIG. 4c and FIG. 4e. The distal section 400 includes two sets of tubes: inlet fluid transfer microtubes 440 and outlet fluid transfer microtubes 442. The inlet fluid transfer tubes 440 direct liquid refrigerant to the distal section of the cryoprobe creating a cryogenic energy delivery region to treat tissue in the vicinity of the probe. These cooling (or active) microtubes are shown in an annular formation. The outlet fluid transfer (or return) microtubes 442 direct liquid refrigerant away from the target site.

FIG. 4b is an enlarged view of the distal end of energy delivery section 400 shown in FIG. 4a. An end cap 443 is positioned at the ends of the inlet microtubes 440 and outlet microtubes 442, defining a fluid transition chamber 444. The transition chamber 444 provides a fluid tight connection between the inlet fluid transfer microtubes and the outlet fluid transfer microtubes. The end cap may be secured and fluidly sealed with an adhesive or glue. In one embodiment, a bushing 446 is used to attach plug 448 to the distal section. Other manufacturing techniques may be employed to make and interconnect the components and are still intended to be within the scope of the invention.

FIG. 4c illustrates an enlarged view of a transitional region 450 in which the plurality of cooling microtubes 440 are fluidly coupled to one or more larger inlet passageways 460 and the return microtubes are fluidly coupled to one or more larger return passageways 452. The return line(s) ultimately direct the liquid refrigerant back to the cryogen source or container such as, for example, container 30 described in FIG. 3 above, and thereby complete the flowpath or loop of the liquid cryogen and without allowing the cryogen to evaporate or escape.

In a preferred embodiment, the inlet line 460 is thermally insulated. Insulation may be carried out with coatings, and layers formed of insulating materials. A preferred insulating configuration comprises providing an evacuated space, namely, a vacuum layer, surrounding the inlet line.

The fluid transfer microtubes may be formed of various materials. Suitable materials for rigid microtubes include annealed stainless steel. Suitable materials for flexible microtubes include but are not limited to polyimide (Kapton®). Flexible, as used herein, is intended to refer to the ability of the multi-tubular distal end of the cryoprobe to be bent in the orientation desired by the user without applying excess force and without fracturing or resulting in significant performance degradation. This serves to manipulate the distal section of the cryoprobe about a curved tissue structure.

In another embodiment flexible microtubes are formed of a material that maintains flexibility in a full range of temperatures from −2000 C to ambient temperature. In another embodiment materials are selected that maintain flexibility in a range of temperature from −2000 C to 1000 C.

The dimensions of the fluid transfer microtubes may vary. Each of the fluid transfer microtubes preferably has an inner diameter in a range of between about 0.05 mm and 2.0 mm and more preferably between about 0.1 mm and 1 mm, and most preferably between about 0.2 mm and 0.5 mm Each fluid transfer microtube preferably has a wall thickness in a range of between about 0.01 mm and 0.3 mm and more preferably between about 0.02 mm and 0.1 mm The present invention provides an increase in the heat exchange area over standard (e.g., smooth) probes. The heat exchange area in one embodiment of the present invention is relatively large because of the multi-tubular nature of the distal end. Depending on the number of microtubes used, the distal end can increase the thermal contact area several times over previous standard distal ends having similarly sized diameters with single shafts. The number of microtubes may vary widely. Preferably the number of microtubes in the shaft distal section is between 5 and 100, and more preferably between 20 and 50.

Figure 6:
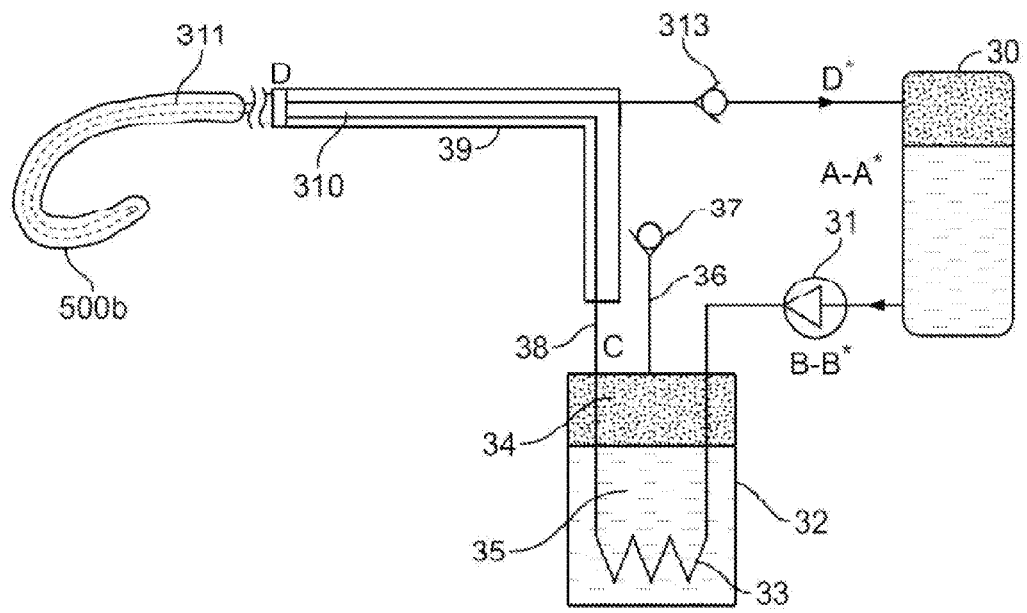
Figure 7:
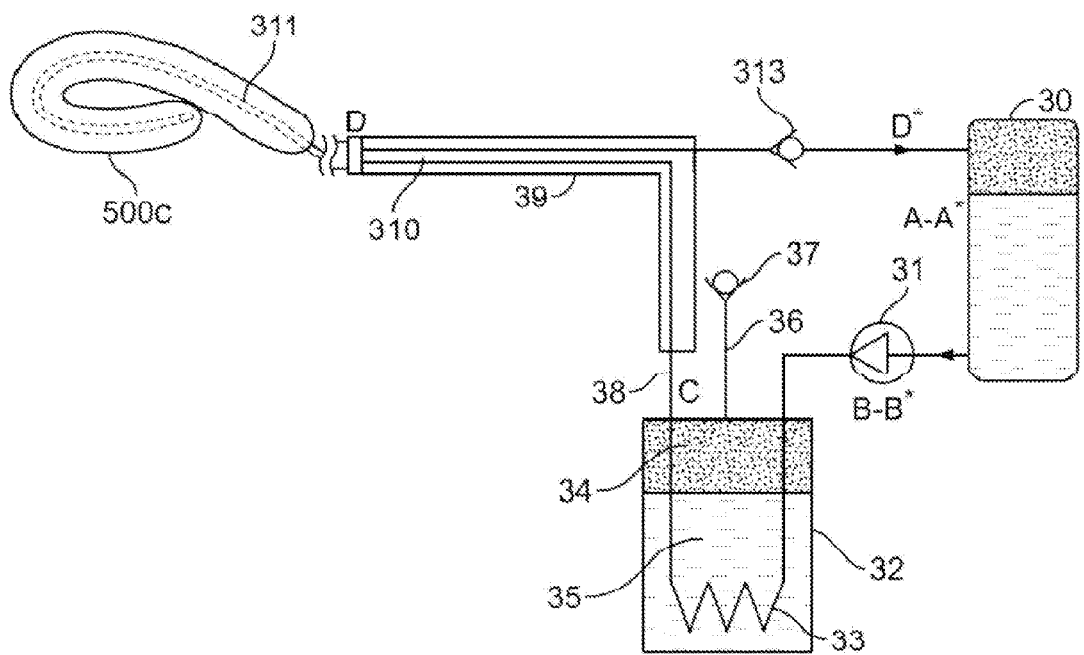

As can be seen in FIGS. 5-7, different shapes of ice structures and iceballs 500a, b, c, may be generated about a flexible multi-tubular distal section 311 of a cryoprobe or cryo catheter. It can be seen that an iceball can be created in a desired shape by bending the distal end in the desired orientation. These shapes may vary widely and include, e.g., an elongate member 500a of FIG. 5, a hook 500b of FIG. 6, a complete loop 500c as shown in FIG. 7, or an even tighter spiral ("fiddlehead fern"). These shapes of the distal free segment can be formed for use in open surgical applications, or formed after delivery to target regions, such as with laparoscopic, robotic, endovascular or even select percutaneous applications. See also International Patent Application No. PCT/US2008/084004, filed Nov. 19, 2008, describing another multitubular cryoprobe.

The capability of the multi-tubular distal end of the cryoprobe extends cryoablation from a rigid needle-like application to nearly any current device used to assist current diagnostic and therapeutic procedures including but not limited to external and internal cardiac applications, endoscopic applications, surgical tools, endovascular uses, subcutaneous and superficial dermatologic applications, radiological applications, and others.

Increased Outer Surface Area

Another embodiment of the present invention increases cryoablation effectiveness by modifying the outer surface of the distal energy delivery section. Increasing the outer surface area that is in thermal contact with the target tissue accelerates the formation of ice structures around the distal energy delivery section, and consequently, enhances the cryoablation treatment efficiency. As will be described herein, the formation of the ice structure or ice ball is enhanced with various structures and designs on the outer surface of the distal section of a cryoablation device (e.g., a stiff-shafted cryoprobe).

Figure 8A:
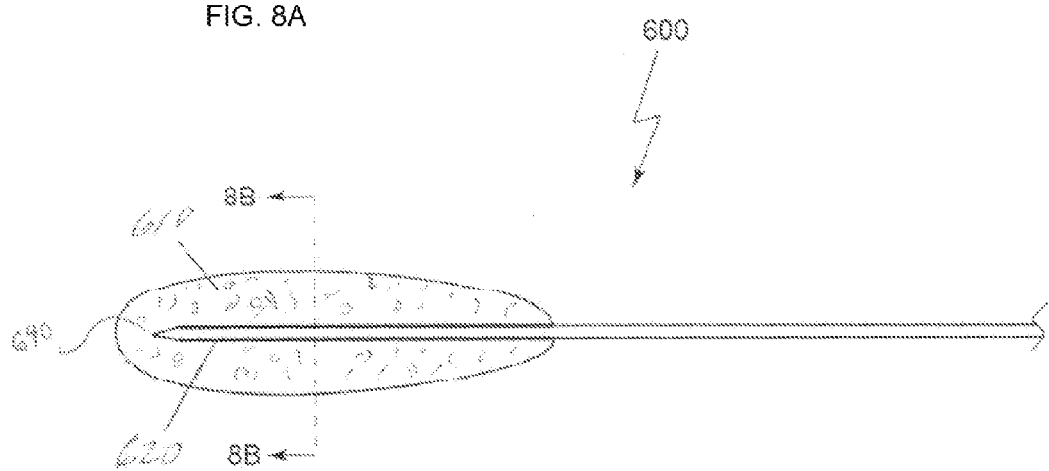
FIG. 8A is a side view of a cryoprobe inserted in a biological tissue.
Figure 8B:
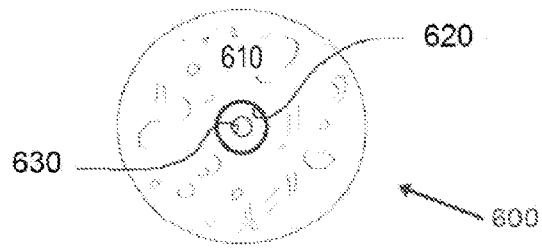
FIG. 8B is a cross sectional view of the cryoprobe and tissue shown in FIG. 8A taken along line 8B-8B.

To better illustrate the heat transfer efficiency, reference is made to FIGS. 8A and 8B. FIG. 8A is a partial side view of a distal energy delivery section 600 of a cryoablation apparatus positioned in a target tissue 610 such as for example a tumor.

FIG. 8B is a cross sectional view of the cryoablation apparatus 600 and tissue 610 taken along line 8B-8B of FIG. 8A. Delivery tube 620 and return flow tube 630 are shown in a concentric or annular configuration. More than one delivery and return tube may be provided. The delivery and return tubes transport the refrigerant to and from the distal tip 640 of the cryoablation apparatus.

The distal energy delivery section 600 is shown in direct contact with the tissue 610 to be treated. Heat is conducted through the wall of the apparatus, and to the tissue 610. Consequently, increasing the outer heat exchange surface area along this region leads to significant improvement of the treatment effectiveness.

Figure 9B:
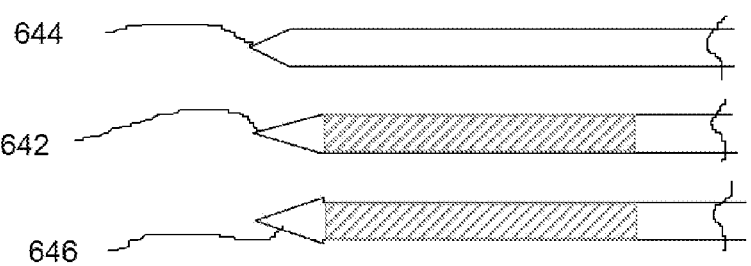
FIG. 9B shows various distal tip shapes of a cryoablation apparatus.
Figure 9A:
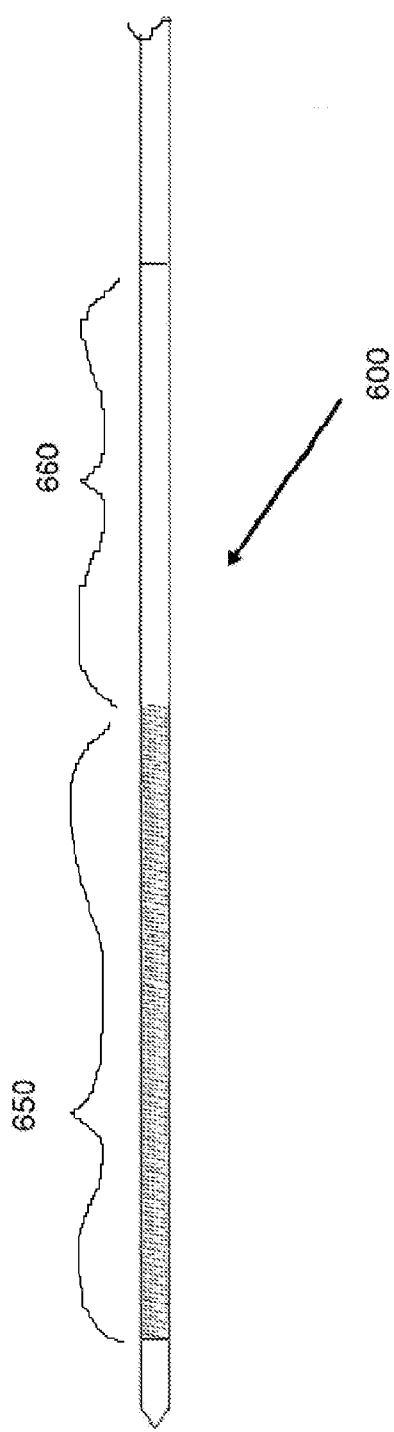
FIG. 9A is a partial side view of an elongate shaft of a cryoablation apparatus having an enhanced heat exchange region and a standard region.

An example of a heat exchange enhanced cryoablation apparatus is shown in FIG. 9A. In particular, a distal section 600 of a cryoablation apparatus comprises a first heat exchange region 650 and a second heat exchange region 660 proximal to the first region 650. Although only two regions are shown, the invention is not so limited. Indeed, multiple heat exchange regions may be disposed along the shaft of the apparatus.

Heat exchange region 650 is shown having a threaded structure. The threads increase the surface area. A wide variety of structures or means may increase the surface area of the enhanced regions including for example threads, ridges, grooves, corrugations, bumps, divots, cuts, slits, texture, and other patterns or coatings. However, as mentioned above, the shape may vary.

An exemplary characteristic dimension or height of a surface enhancement structure is about 0.01 inches from the valley to the peak of the structure (e.g., corrugation, ridges, threads, etc.) Additionally, it is desirable that the size of structure is sufficiently small such that the shaft may be smoothly advanced into tissue without too much friction.

In one embodiment, a plastic sleeve is positioned over the elongate shaft and the assembly is advanced as one unit into the tissue. The low friction sleeve or cover may be removed/withdrawn after the shaft is properly positioned in the tissue. Alternatively, and with reference to FIG. 9B, the needle tip can be configured to have a shallower bevel angle 642 for easier penetration of firm tissues than a standard tip 644. For example the bevel angle of 642 is preferably less than 45 degrees, or less than 30 degrees from the shaft axis. Additionally, the needle tip can be configured to have a slightly larger diameter tip 646 to allow the probe segments following the tip to slide into the tissue with less friction.

The distal heat exchange region 650 is shown having a length greater than that of the proximal heat exchange region 660. The heat exchange regions may have different or similar lengths and patterns. In one embodiment, the length of the first heat exchange region ranges from 20 to 60 mm The distal energy delivery section of the cryoablation apparatus may have a heat exchange efficiency which varies with length.

Figure 9C:
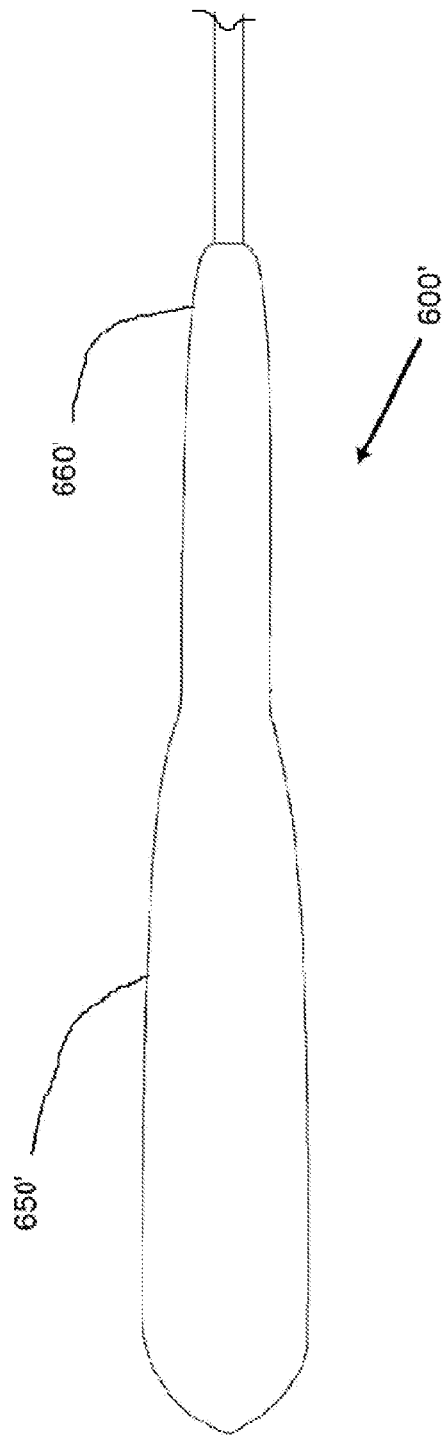
FIG. 9C is a view of an ice structure formed around the elongate shaft of the cryoablation apparatus shown in FIG. 9A.

FIG. 9C illustrates the anticipated formation of an ice structure 650', 660' around the distal energy delivery section 600' of a cryoablation apparatus in accordance with one embodiment of the present invention. When a distal energy delivery section as shown and described in FIG. 9A is submerged in, for example, a water bath, and the apparatus is activated, an ice structure or ball 650', 660' is rapidly formed around the threaded heat exchange surface of cryoprobe tip 600'.

The shape of the ice structure corresponds to the design of heat exchange regions.

A first ice structure corresponds to the first heat exchange region, and a second ice structure corresponds to the second heat exchange region. In the predicted example shown in FIG. 9C, the ice structure 650' is enlarged as compared to ice structure 660'. The diameter and the volume of ice formed in the surface enhanced region 650' is greater than that of the standard energy deliver region 660'.

The cryoablation apparatus 600 may be designed to form specific ice structures corresponding to specific tissue or shapes of tissues and tumors. Examples of shapes include round, oval, dog bone, spheroid, cylindrical, etc. An oval shaped cavity, for example, may be filled and treated with an oval shaped ice structure. An oval structure may be formed with, for example, three consecutive heat exchange regions along an elongate distal energy delivery section including a first ridgeless region, a second surface area enhanced region (e.g., outer threads), and a third ridgeless or smooth outer surface area. Consequently, the ice formed would have an enlarged center section corresponding to the second heat exchange enhanced region bounded by two smaller diameter ice structures. Indeed, a wide range of ice structures and shapes may be provided by varying the outer surface of the distal energy delivery section lengthwise.

FIGS. 9D-9G show various types of heat exchange regions and their corresponding anticipated ice structure.

Figure 9D:
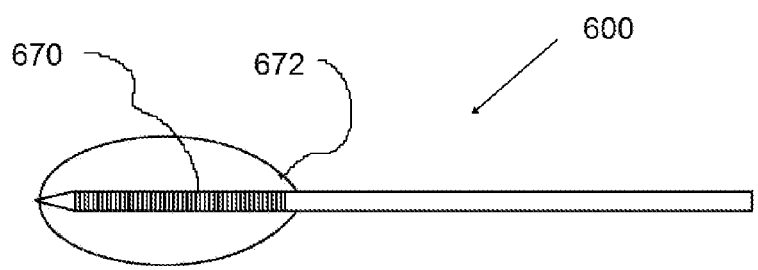
FIGS. 9D-9G show various types of heat exchange regions for a cryoablation apparatus.

FIG. 9D shows a distal section 600 of a cryoablation apparatus including an energy delivery region 670. The heat exchange region comprises a regular pattern of corrugations lengthwise along the shaft. An oval shaped ice structure 672 is anticipated to be formed.

Figure 9E:
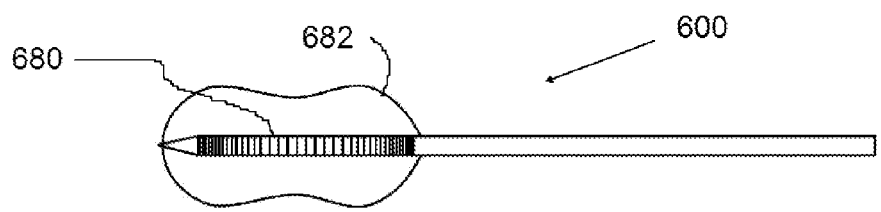

FIG. 9E shows another distal section 600 of a cryoablation apparatus including a heat exchange region 680 having an irregular pattern of corrugations. In particular, the density of corrugations varies along the length of the shaft. The density of corrugations is lowest in an intermediate or middle location of the heat exchange region 680. A peanut or dog bone shaped ice structure 682 is anticipated to be formed.

Figure 9F:
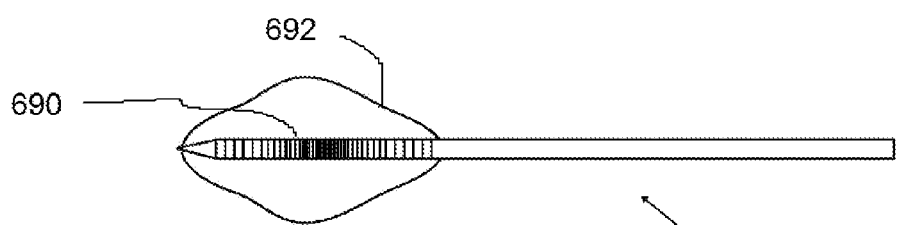

FIG. 9F shows another distal section 600 of a cryoablation apparatus including a heat exchange region 690 having an irregular pattern of corrugations. In particular, the density of corrugations is highest in the intermediate or middle location of the heat exchange region 690. A diamond shaped ice structure 692 is anticipated to be formed.

Figure 9G:
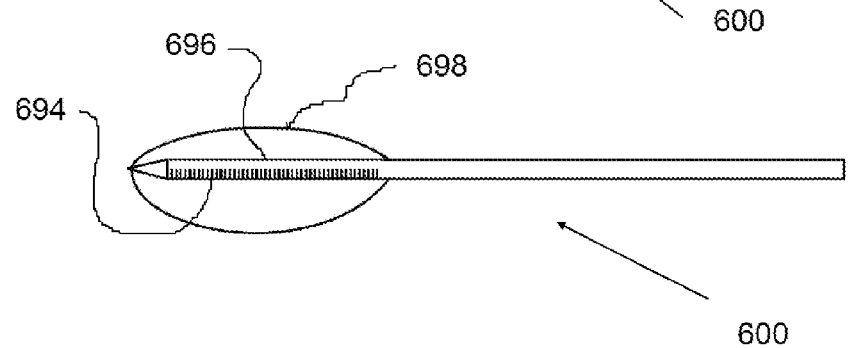

FIG. 9G shows another distal section 600 of a cryoablation apparatus including a first heat exchange region 694, a second heat exchange regions 696 and its corresponding ice structure 698. The ice structure is shown having a non-symmetrical shape about the shaft axis.

In this another embodiment the first heat exchange region 694 corresponds to a first arcuate segment of the energy-delivery section of the elongate shaft and the second heat exchange region corresponds to a second arcuate segment of the energy-delivery section of the elongate shaft such that the heat exchange efficiency varies about the circumference of distal energy-delivery section of the elongate shaft. The first heat exchange region 694 is shown having a greater surface area than that of the second heat exchange region 696. The outer surface of the first heat exchange region 694 is shown having corrugations in a regular repeating pattern. However, as described above, the pattern may vary. The pattern may increase or decrease in density, size, and shape. Examples of shapes include without limitation ridges, grooves, corrugations, and threads.

Additionally, the first heat exchange region 694 is shown spanning about 50% of the circumference of the shaft. However, the span may vary. Preferably, the radial span of the first heat exchange region is between ¼ to ¾ of the circumference of the distal energy-delivery section. The second heat exchange region is shown being smooth. However, it too may have various patterns, shapes, etc.

In view of the above, the energy delivery section may include multiple heat exchange regions along its length, circumference, or any combination therefore. For example, a first arcuate segment with an enhanced heat transfer texture may extend axially for a part of the length (or the entire length) of the distal energy-delivery section.

EXAMPLES

Figure 10A:
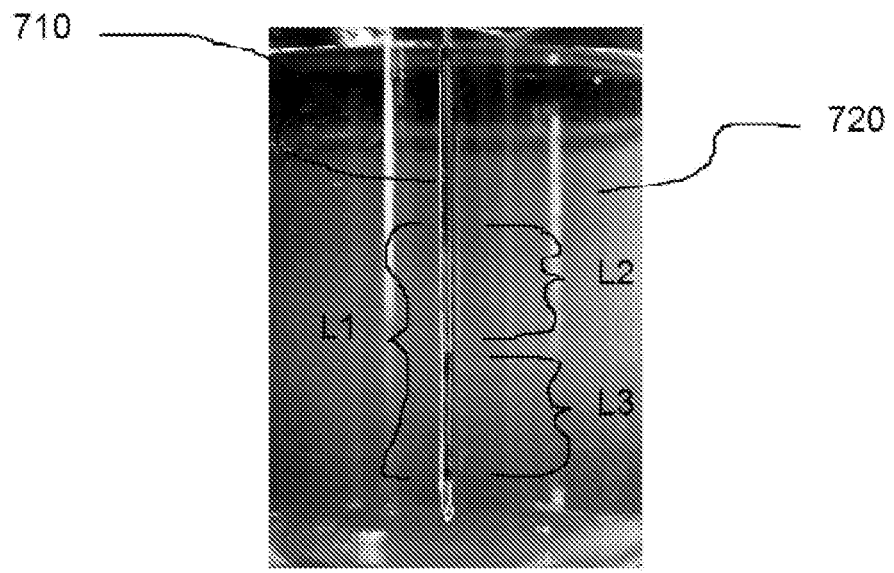
FIG. 10A is an illustration of an experimental set up using a cryoablation apparatus having an enhanced heat exchange region.
Figure 10B:
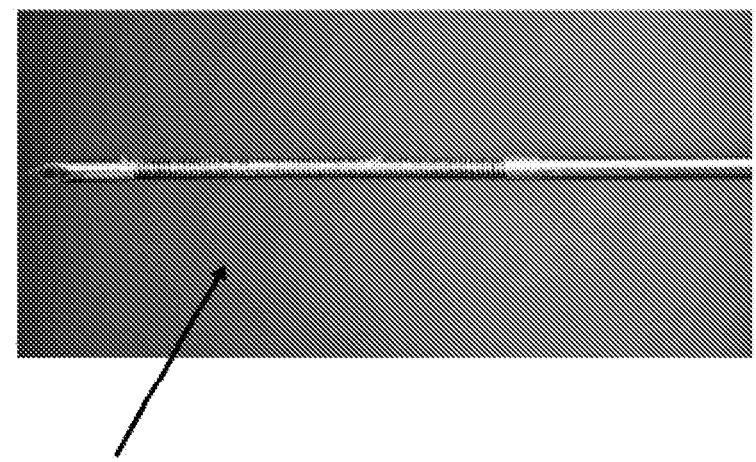
FIG. 10B is a side view of the cryoablation apparatus used in the experiment setup depicted in FIG. 10A.
Figure 11:
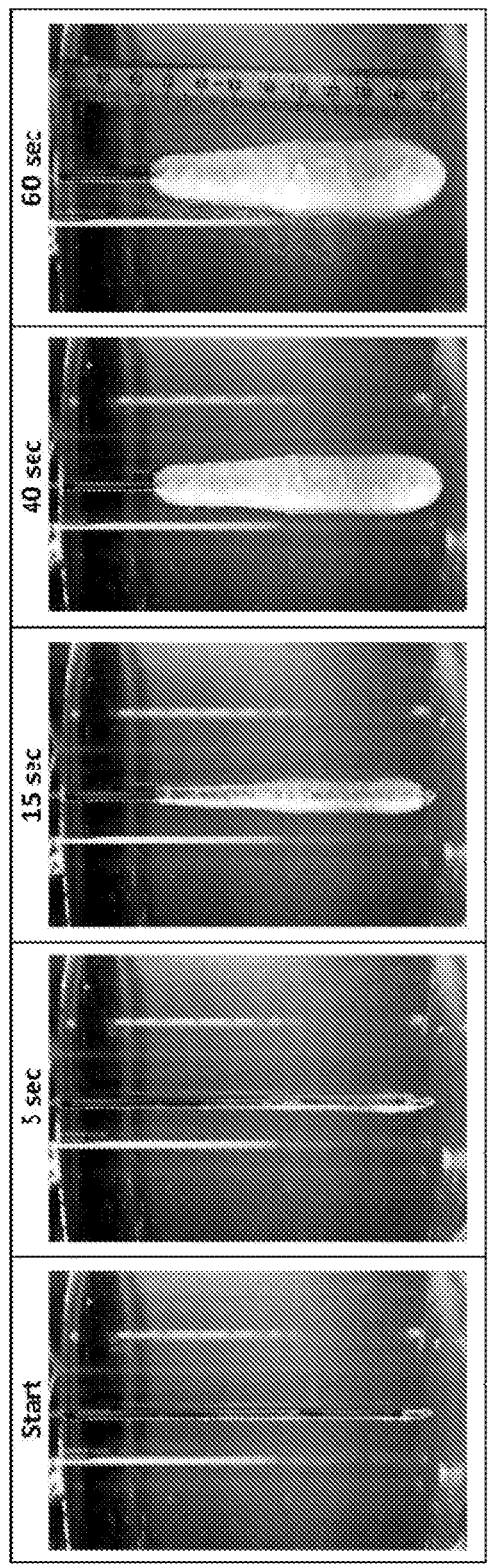
FIG. 11 is a first data set illustrating the formation of an ice structure over time using the experimental setup shown in FIG. 10A.
Figure 12:
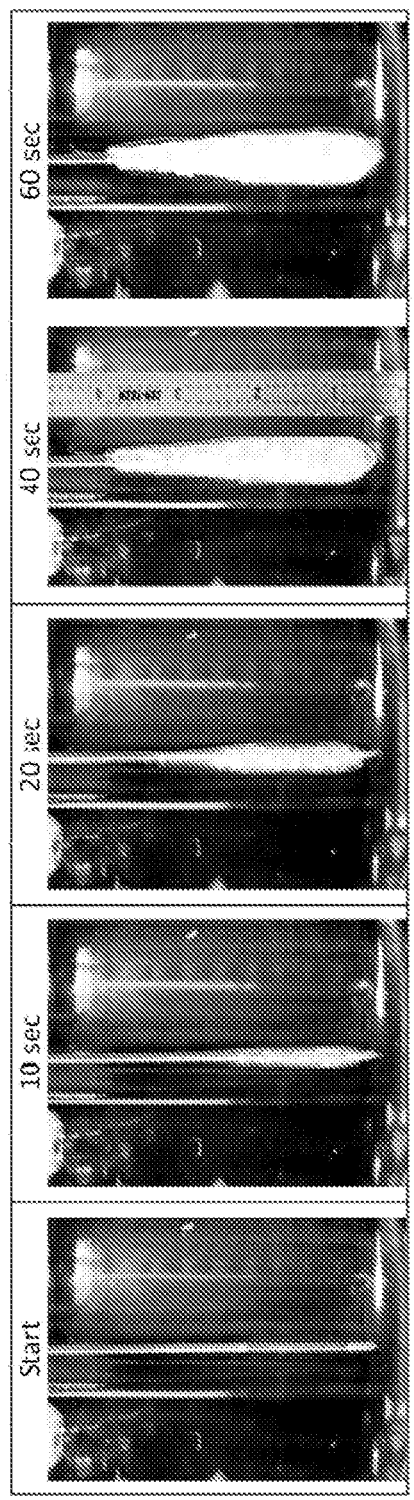
FIG. 12 is a second data set illustrating the formation of an ice structure over time using the experimental setup shown in FIG. 10A.

FIGS. 10-12 demonstrate ice structure formation using an enhanced heat exchange area. In particular, a cryoablation apparatus comprised a stainless steel elongate shaft 710 having a diameter of 2.4 mm The shaft included an energy-delivery region L1 of about 8 cm. The energy delivery regions included a first and a second heat exchange area or region. Region L2 comprised a smooth surface (e.g., standard). Region L3 comprised an enhanced surface as described further below. Each of the sections L2 and L3 had a length of about 4 cm. The overall length of the freeze zone was about 8 cm, which corresponds to the length of the energy delivery section L1.

The L3 surface enhancement structure was achieved by making the needle slightly "corrugated" as shown in FIG. 10B. The size of the corrugations was about 0.01 in.

Given the size of the corrugation, the surface area of region L3 may be computed. The calculated surface enhancement is about 60%. This implies that the 2.4 mm diameter shaft has an increased heat exchange efficiency, and in particular it ought to be able to perform equivalently to a larger (e.g., roughly 3.8 mm) diameter shaft. This also translates into faster achievement of target temperatures within a tissue volume which covers the entire tumor volume. Additionally, this implies that a target volume of tissue necrosis can be achieved with fewer cryoprobes having enhanced surface area. The data below confirms this improvement.

FIGS. 11 and 12 show performance of a cryoablation apparatus during two 60 second freeze cycles in a water bath at two different temperatures. With reference to FIG. 11, Test No. 1, the cryoprobe described above in connection with FIG. 10A was submerged in a 25° C. water, and activated for 60 seconds. This corresponds to about 50 W of power load.

At 15 seconds an ice structure is clearly formed. The iceball at 15 sec of freeze shows that the diameter in the enhanced region (about 7.5 mm) is clearly larger than that in the standard region (about 5 mm) The diameter is roughly 2.5 mm (or 50%) larger in the area with the enhanced surface.

At 60 seconds, the iceball of freeze shows that the diameter in the enhanced region (about 23 mm) is clearly larger than that in the standard region (about 16 mm) The diameter is approximately 7 mm (or 45%) larger in the area with the enhanced surface L3 than that of the standard region L2.

With reference to FIG. 12, Test No. 2, the cryoprobe described above in connection with FIG. 10A was submerged in a 36° C. water, and activated for 60 seconds. This corresponds to about 70 W of power load.

At 20 seconds an ice structure is clearly formed. The iceball at 20 sec of freeze shows that the diameter in the enhanced region (about 10 mm) is clearly larger than that in the standard region (about 4 mm) The diameter is roughly 6 mm (or 150%) larger in the area with the enhanced surface. It also appeared to be much colder (cold ice is opaque, and not transparent).

At 60 seconds, the iceball of freeze shows that the diameter in the enhanced region (about 16 mm) is clearly larger than that in the standard region (about 11 mm) The diameter is approximately 5 mm (or 45%) larger in the area with the enhanced surface L3 than that of the standard region L2. The ice in the enhanced region also appeared to be much colder (cold ice is opaque, and not as transparent).

FIGS. 13A-D are predicted examples illustrating formation characteristics of lethal isotherms covering a tumor volume when multiple cryoablation probes are utilized. In particular, FIGS. 13A,C shows the estimated cross-sectional surface area generated by 3 standard smooth cryoprobes using JT cooling versus that from enhanced surface cryoprobes using a SPLC cooling FIGS. 13B,D. Since the rate of volumetric ice formation begins to approach a steady-state after several minutes, the faster forming lethal zone of SPLC at 5 min is projected to be similar to a 10 minute ablation volume by smooth surfaced probes using standard JT cryotechnology. At least a 50% reduction in overall procedure time is predicted to be achieved by the greater facilitated heat exchange with surrounding tissues using enhanced surface area and a SPLC cryogenic system with greater cooling capacity as described herein.

Figure 14A:
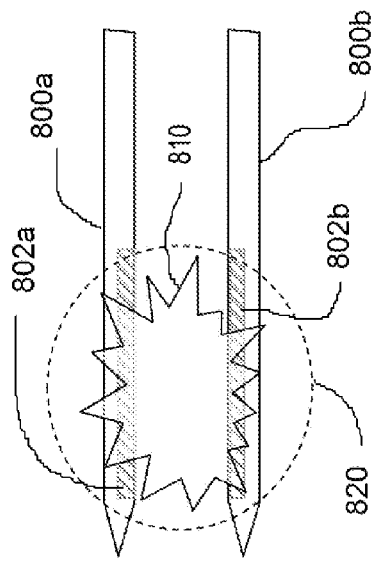
FIG. 14A is a partial top view of two cryoprobes in accordance with one embodiment of the invention positioned in a tumor.
Figure 14B:
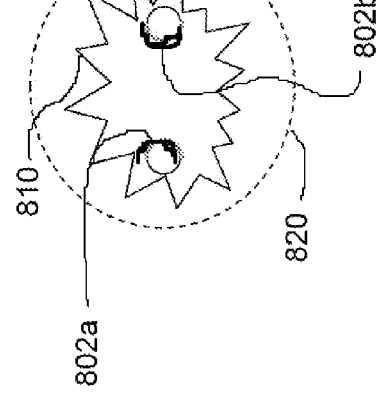
FIG. 14B is an end view of the two cryoprobes and tissue shown in FIG. 14A.

FIGS. 14A and 14B show a partial top view and end view of two cryoablation devices 800a, 800b inserted in a tumor 810 in accordance with one embodiment of the invention. Each cryoablation apparatus includes a first heat exchange region 802a, 802b. The heat exchange regions 802a, 802b extend along the shaft spanning about 50% of its outer circumference. The combination of the two regions bracket the small irregular shaped tumor 810. The heat exchange regions 802a, 802b are turned towards the central portion of the tumor 810, resulting in a more circumferential lethal isotherm 820, as well as allowing greater probe spacing toward the edges of the tumor.

Figure 15A:
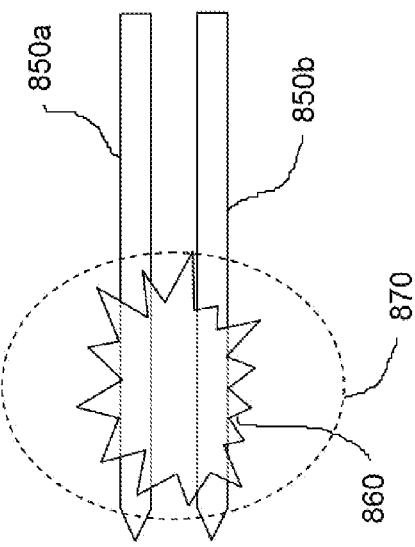
FIG. 15A is a partial top view of two standard cryoprobes positioned in a tumor.
Figure 15B:
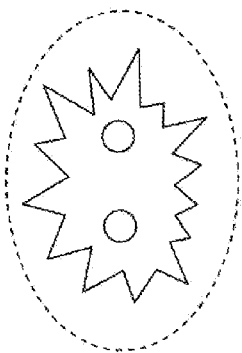
FIG. 15B is an end view of the two cryoprobes and tissue shown in FIG. 15A.

FIGS. 15A and 15B show a partial top view and end view of two standard cryoablation devices 850a, 850b inserted in a small irregular tumor 860. The cryoablation devices are shown bracketing the tumor. The shafts of the cryoablation devices are smooth surfaced needles and lack multiple regions or patterns. The needles 850a, 850b require no greater than 2 cm. spacing and 1 cm. from the tumor margin, yet result in an ovoid lethal isotherm 870 that extends well beyond the tumor margin and destroys much greater volume of adjacent normal adjacent tissue than the cryoprobe described in FIGS. 14A and 14B. This is undesirable.

The heat exchange apparatuses described herein increase the heat transfer and formation of colder ice within shorter times. Additionally, the shape of the ice structure may be designed in advance by incorporating various structures into the shaft. Shape-specific ice structures may be used to fill and treat cavities, organs and tissues.

The cryoablation apparatus has a wide range of therapeutic applications. Examples of applications include but are not limited to the following: laparoscopic, endovascular and percutaneous procedures.

In connection with laparoscopic and/or robotic procedures, the flexible distal segments of the cryoprobe or cryo catheter (e.g., the cryoprobe described in FIGS. 5-7) are formed after insertion through transcutaneous trocars. These standard trocars are currently utilized to gain access into body cavities, such as the chest, abdomen or pelvis using standard techniques. Once direct visualization has been achieved by laparoscopic cameras, the flexible tipped cryoprobe or cryocatheter can be inserted in another port to achieve access to the body cavity. Alternatively, the cryoprobe/cryocatheter can be directly inserted using a slightly larger sheath as needed. Using similar internal wire configuration that allows endoscopes or vascular catheters to form a loop, the flexible tipped cryoprobe/cryocatheter can be shaped in a range of positions from a slight bend to a coil. Under these configurations, the inner side of the loop or coil intending to contact the tissue would have the enhanced surface area for faster transmission of target temperatures into the adjacent tissue to be treated.

In connection with endovascular procedures, transmission of target temperatures into adjacent tissues may involve direct contact of a flexible tipped catheter, such as the wall of the heart's left atrium to disrupt electrical foci causing atrial fibrillation. Alternatively, direct contact with a vessel wall may be considered for adjacent nerve ablation, such as the renal nerve traveling within, or surrounding, the wall of the renal artery. Standard vascular access, or Seldinger techniques, would be used to likely enter the femoral and/or brachial artery, followed by sheath placement to the endovascular target region. The enhanced surface area cryocatheter would then be deployed to this area and the enhanced surface area and engaged with the target tissue.

In connection with percutaneous procedures, most involve the use of image guided placement of stiff-shafted cryoprobes. This may be done under either US, CT or MR-guidance in associated imaging suites. Following identification of the target region or tumor, an initial thin localization needle (e.g., 20 gauge) can be placed into the tumor to assess the optimal access trajectory and avoidance of intervening crucial structures (e.g. bowel). One or more cryoprobes can then be inserted to maintain a distribution within the tumor that will generate sufficient cytotoxic ice to cover the overall tumor volume. While this generally requires a 10 min freeze of a minimum number of probes equal to tumor diameter (e.g., 4 smooth surfaced J-T cryoprobes for a 4 cm diameter tumor), enhanced surface cryoprobes could be used to markedly reduce the freeze time and/or the required number of cryoprobes. This can be directly validated by the benefits of cryoablation having a visible 0° C. ice margin on either US, CT or MR imaging. In some cases, multiple freezes are applied.

Following completion of the second freeze, the thaw phase would also be expedited by the enhanced surface area. Namely, a warmed cryogen fluid sent through the cryoprobe tip would break the frozen seal between the cryoprobe surface and adjacent tissue to "unstick" the cryoprobe even faster.

It will be understood that some variations and modification can be made thereto without departure from the spirit and scope of the present invention.

We claim:

1. A cryoablation method for applying cryoenergy to tissue comprising the steps of:
    driving a liquid refrigerant along a first flowpath through a first cryoprobe having an energy delivery distal section, wherein said liquid refrigerant remains in a liquid-only state along the first flowpath;
    positioning said energy delivery distal section of said first cryoprobe in a vicinity of said tissue;
    transferring cryoenergy to said tissue to freeze said tissue through a first heat exchange area extending along said energy delivery distal section of said first cryoprobe; and wherein said first heat exchange area includes only one tubular-shaped outermost wall defining a passageway for accommodating the liquid refrigerant being transported through the energy delivery distal section, and said one tubular-shaped outermost wall further comprises an exterior surface formed of a discrete surface area enhancing structure extending radially and outwardly therefrom defining peaks and valleys along the exterior surface of the one tubular-shaped outermost wall, thereby increasing the surface area of the first heat exchange area along the energy delivery distal section of the first cryoprobe and wherein the first flowpath commences at a refrigerant source, continues through the first cryoprobe, through the energy delivery distal section, and returns to one of the refrigerant source or a reservoir, and wherein the refrigerant remains in the liquid only state during an entire first flowpath and during the step of transferring cryoenergy to the tissue.

2. The method of claim 1 wherein the first cryoprobe comprises a second heat exchange region, wherein the step of transferring cryoenergy to said tissue through the first heat exchange area comprises delivering energy through a first surface area, said first surface area being larger than a second surface area of the second heat exchange region.

3. The method of claim 2 wherein the first surface area is at least 1.1 to 3.0 larger than the second surface area.

4. The method of claim 1 wherein the peaks and valleys of the first heat exchange area define ridges.

5. The method of claim 1 wherein the positioning step is carried out through one device selected from the group consisting of an endoscope, a visualization device and a steering device.

6. The method of claim 1 further comprising inserting at least a second cryoprobe in said tissue.

7. The method of claim 6 further comprising manipulating at least one of the first heat exchange region of the first cryoprobe and the first heat exchange region of the second cryoprobe such that a second heat exchange region of the first cryoprobe faces the second heat exchange region of the second cryoprobe.

8. The method of claim 1 wherein said peaks and valleys define a structure selected from the group consisting of ridges, grooves, corrugations, and threads.

9. The method of claim 8 wherein the peaks have a characteristic height in a range of 2 mm to 5 mm.

10. The method of claim 1 wherein said energy delivery distal section is rigid.

11. The method of claim 10 wherein the energy delivery distal section comprises a beveled tip.

12. The method of claim 1 wherein an inner surface of the first heat exchange area is substantially smooth and ridgeless.

13. The method of claim 1 wherein the first heat exchange area has a first length ranging from 1 cm to 6 cm.

14. The method of claim 1 wherein said discrete surface area enhancing structure has a regular pattern.

15. The method of claim 14 wherein the positioning step comprises advancing the first cryoprobe percutaneously.

16. The method of claim 1 wherein the positioning step comprises advancing the first cryoprobe into a tumor.

17. The method of claim 1 wherein the liquid refrigerant is transported to and from the refrigerant source.

* * * * *